United States Patent
Silva-Craig et al.

(10) Patent No.: US 7,593,972 B2
(45) Date of Patent: Sep. 22, 2009

(54) APPLICATION SERVICE PROVIDER BASED REDUNDANT ARCHIVE SERVICES FOR MEDICAL ARCHIVES AND/OR IMAGING SYSTEMS

(75) Inventors: Milton Silva-Craig, Arlington Heights, IL (US); Greg Angst, Cary, IL (US); Thanos Karras, Mount Prospect, IL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 1099 days.

(21) Appl. No.: 09/681,471

(22) Filed: Apr. 13, 2001

(65) Prior Publication Data

US 2002/0152231 A1    Oct. 17, 2002

(51) Int. Cl.
*G06F 12/00* (2006.01)
*G06F 17/30* (2006.01)

(52) U.S. Cl. .................. 707/204; 707/200; 707/203
(58) Field of Classification Search .................. 707/10, 707/204, 9, 202; 709/224, 203
See application file for complete search history.

(56) References Cited

U.S. PATENT DOCUMENTS

| | | | | |
|---|---|---|---|---|
| 4,958,283 A | * | 9/1990 | Tawara et al. ............ 707/104.1 |
| 5,867,821 A | * | 2/1999 | Ballantyne et al. ............ 707/10 |
| 5,893,073 A | * | 4/1999 | Kasso et al. ................... 705/8 |
| 5,902,981 A | * | 5/1999 | Dethloff ..................... 235/375 |
| 5,950,207 A | * | 9/1999 | Mortimore et al. ....... 707/104.1 |
| 6,038,564 A | * | 3/2000 | Sameshima et al. ........... 707/10 |
| 6,073,209 A | * | 6/2000 | Bergsten ..................... 707/204 |
| 6,081,809 A | * | 6/2000 | Kumagai ................. 707/104.1 |
| 6,141,699 A | * | 10/2000 | Luzzi et al. ................... 707/10 |
| 6,221,010 B1 | * | 4/2001 | Lucas ......................... 600/300 |
| 6,263,330 B1 | * | 7/2001 | Bessette ......................... 707/4 |
| 6,338,433 B1 | * | 1/2002 | Drexler ................. 235/462.01 |
| 6,675,271 B1 | * | 1/2004 | Xu et al. ...................... 711/161 |
| 6,678,703 B2 | * | 1/2004 | Rothschild et al. .......... 707/201 |
| 6,678,764 B2 | * | 1/2004 | Parvulescu et al. ............ 707/10 |
| 2002/0083192 A1 | * | 6/2002 | Alisuag ...................... 709/237 |

* cited by examiner

*Primary Examiner*—Baoquoc N To
(74) *Attorney, Agent, or Firm*—McAndrews, Held & Malloy, Ltd.; Peter J. Vogel; Michael A. Dellapenna

(57) ABSTRACT

A preferred embodiment of the present invention provides a method and system for application service provider based redundant archive services for medical archives and/or imaging systems. In a preferred embodiment, the system comprises a data source providing medical data, a status monitor for controlling the transfer of the medical data from the data source to a remote data store, and a remote data store receiving the medical data and storing the medical data. Additionally, the remote data store may restore the medical data to the data source. Also, the remote data store preferably may transfer the medical data to a second data source. Preferably, the remote data store is an application service provider.

9 Claims, 4 Drawing Sheets

APPLICATION SERVICE PROVIDER BASED REDUNDANT ARCHIVE SERVICES FOR MEDICAL ARCHIVES AND/OR IMAGING SYSTEMS

BACKGROUND OF INVENTION

The preferred embodiments of the present invention generally relate to data storage and retrieval systems, and in particular relate to a method and system for Application Service Provider (ASP) based redundant archive services for medical archives and/or imaging systems.

Healthcare practitioners, such as physicians, nurses, assistants, or technicians, for example, employ medical data for diagnosis and treatment of patients. For example, healthcare practitioners may use medical data such as medical images, medical reports, applications, and other data, for example, to diagnose and treat patients. Medical data may be obtained from direct examination, from other healthcare practitioners, from medical diagnostic equipment, and/or from other sources, for example.

Medical data may be stored in a local database at a healthcare facility, such as a hospital, clinic, doctor's office, or other medical office, for example. Storage of medical data in a local database may enable the medical data to be used in diagnosis and treatment of patients. That is, storage of medical data in a local database may improve access and retrieval of data for diagnosis and treatment. Medical data may be stored in a local database such as a Picture Archiving and Communication System (PACS).

A PACS may be used to obtain, store, and distribute electronic images, such as electronic medical diagnostic images. A PACS may allow images to be archived in electronic form in a central location on site. A PACS may also allow images to be shared among different users because the images are locally centralized and able to accessed at numerous points on site. Convenient access to patient data through a PACS may improve individual hospital workflow by eliminating the need to physically transfer images and by providing multiple viewing stations for imaging results.

Typically, data stored in a PACS is stored as DICOM data. DICOM stands for Digital Imaging and Communications in Medicine. DICOM is a standard for image and information transmission. DICOM relates to the transfer of electronic data between medical diagnostic and imaging systems. The DICOM protocol may be employed in communication between medical devices and a PACS. The DICOM standard enumerates a command set, data formats, interface specifications, communication protocols, and command syntax. The DICOM standard does not specify details of implementation.

Increasingly, healthcare practitioners are relying on the PACS and other digital environments for diagnosis and treatment of patients. As customers become more reliant on digital environments, there is need for greater backup and redundancy capabilities for digital medical data. There is a need for a source that satisfies the need for greater backup and redundancy through cost-effective and easily managed methods.

Centralized access to medical data may also improve diagnosis and treatment of patients through ease of retrieval by multiple users and/or multiple locations. In the field of computers, Application Service Providers (ASPs) have been employed to allow for centralized access and storage of data. ASPs operate as hosts for data and applications. Typically, ASPs maintain applications and data in an off-site data center. ASPs have been hired by companies in the field of computers to manage data and computer applications. Companies may access data and applications via an ASP. Typically, in the computer field, companies remotely access data and applications via an ASP central data location.

In the field of computers, ASPs may offer several desirable services, such as secure data storage, data backup, and redundant systems. Because ASPs offer such services, a customer of an ASP may not have to incur additional expenses for its own security, backup, and storage systems. In addition to functioning as a remote database, ASPs may host a number of applications that may be activated or accessed remotely by customers. By concentrating computing power and maintenance at the ASP, the ASP may offer continuous access to and support of the applications and alleviate the need for the customer to purchase and maintain its own expensive computer equipment.

For example, ASPs may provide installation, management, and support of applications and storage of data for many remote clients. Client data may be stored at a remote data center. Data may be retrieved from a remote data center via a communications medium such as the Internet or a private network. Additionally, ASPs may deliver applications such as email systems, resource planning systems, customer relationship management systems, human resource management systems, and proprietary applications to remote clients.

Access to medical data may improve diagnosis and treatment of patients by healthcare practitioners. For example, healthcare practitioners may employ medical diagnostic reports and images in addition to direct examination of the patient by the healthcare practitioner. Additionally, multiple healthcare practitioners may access medical data for diagnosis and treatment of patients. Thus, there is a need for access to medical data to aid in medical diagnosis and treatment of patients by supplementing the healthcare practitioner's examination.

Additionally, reliability of access, storage, and/or retrieval of medical data may improve diagnosis and treatment of patients by healthcare practitioners. That is, if medical data is lost or corrupted, diagnosis and/or treatment of a patient may be impaired without reliable retrieval of medical data. Reliable access to medical data may help to ensure that patients may be accurately and timely diagnosed and treated by healthcare practitioners. For example, protection against corruption or loss of medical data ensures that the medical data may be available for use by a healthcare practitioner in diagnosing and/or treating a patient. Thus, there is a need for reliability in the storage of medical data to improve diagnosis and treatment of patients.

Currently, backup systems for local databases in healthcare facilities are typically local backup systems. Local backup systems may be expensive for individual healthcare facilities. Additionally, local backup systems may require time, money, and personnel to maintain. Thus, there exists a need for a centralized archive for medical data.

Thus, there is a need for redundant secure storage to guard against data loss. That is, redundant secure storage reduces the likelihood that a patient will have to return to the healthcare facility and be re-examined to replace images and other examination data in the event of data loss and/or corruption. Additionally, there is a need for a system that can repair or replace lost and/or corrupted data in the event of data loss or system failure. That is, a system that can repair or replace data in the event of data loss and/or corruption reduces the probability that a patient will be reexamined at a healthcare facility to replace lost and/or corrupted images and other examination data. There is also a need for easier data manipulation and/or preservation between medical diagnostic system upgrades. For example, there is a need for a system to reduce manual transfer and/or re-creation of data, applications, and/or operating system information between an old medical diagnostic or storage system and a new or replacement system.

Thus, a need exists for storage of data to improve reliability of access to medical data for patient diagnosis and treatment. Additionally, there is a need for retrieval of medical data to improve reliability of access to medical data in the event of data corruption or loss. There is a further need for ease of copying data to improve installation and configuration of medical diagnostic and/or storage systems.

SUMMARY OF INVENTION

A preferred embodiment of the present invention provides a method and system for application service provider based redundant archive services for medical archives and/or imaging systems. In a preferred embodiment, the system comprises a data source providing medical data, a status monitor for controlling the transfer of the medical data from the data source to a remote data store, and a remote data store receiving the medical data and storing the medical data. Preferably, the medical data is transferred at a definable interval. In a preferred embodiment, the definable interval may be a timed interval, an event-based interval, and/or a manual interval. Additionally, the remote data store may restore the medical data to the data source. Also, the remote data store preferably may transfer the medical data to a second data source. Preferably, the remote data store is an application service provider. The system may also include a status monitor for monitoring operations between the data source and the remote data store. Additionally, the system may include an access authenticator for authenticating access to the remote data store.

In a preferred embodiment, the method includes transferring medical data from a data source to a remote data store and storing the medical data at the remote data store. Preferably, the medical data is stored at the remote data store in a directory corresponding to the data source. In a preferred embodiment, the medical data at the remote data store may be restored at the data source. Additionally, the medical data at the remote data store may be copied to a second data source.

DETAILED DESCRIPTION

Figure 1:
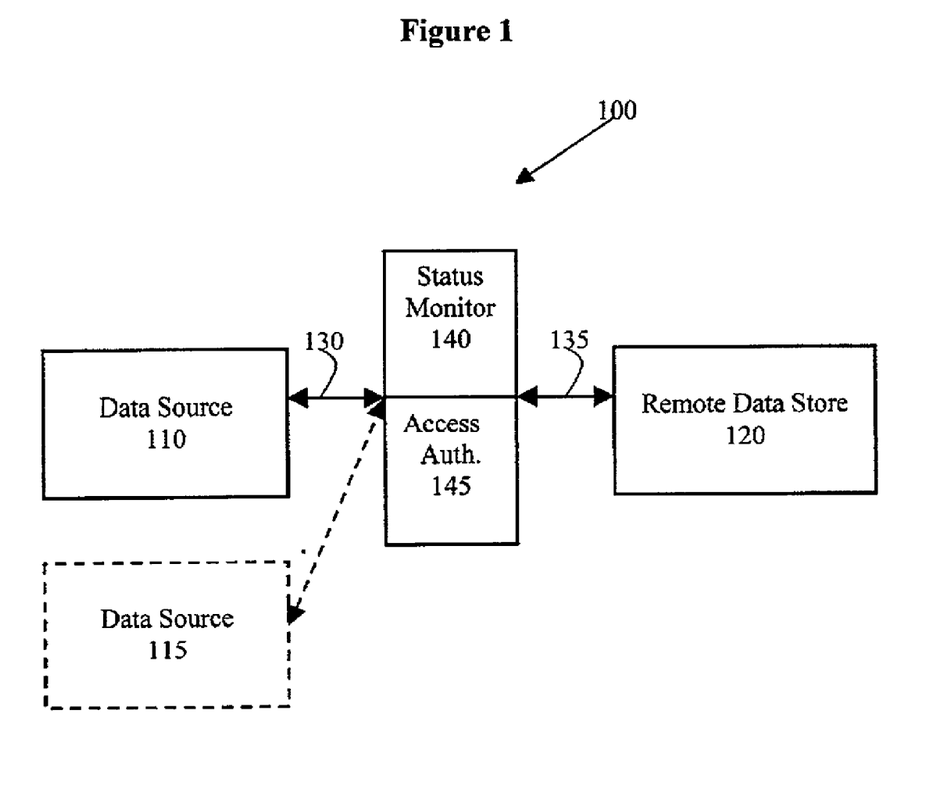
FIG. 1 illustrates a centralized remote data storage and retrieval system for archiving and restoring data in accordance with a preferred embodiment of the present invention.

FIG. 1 illustrates a centralized remote data storage and retrieval system 100 for archiving and restoring data in accordance with a preferred embodiment of the present invention. The centralized remote data storage and retrieval system 100 includes a plurality of subsystems, such as a data source 110, a remote data store 120, a front-end connection 130, a back-end connection 135, a status monitor 140, and an access authenticator 145.

The front-end connection 130 connects the data source 110 to the status monitor 140 and the access authenticator 145. That is, the front-end connection 130 facilitates communication between the data source 110 and the status monitor 140 and the access authenticator 145. The back-end connection 135 connects the status monitor 140 and the access authenticator 145 to the remote data store 120. Preferably, the front-end connection 130 and the back-end connection 135 compose a data source/data store connection for bi-directional communication between the data source 110 and the remote data store 120.

Preferably, the data source 110 is a picture archiving and communications system (PACS), a medical diagnostic imaging system, a database system, a computer system, a server, a hard disk drive, a terminal, or other medical data storage system, for example. Preferably, the data source 110 includes memory, such as a hard disk drive, a CD-ROM drive, a DVD drive, a floppy disk drive, a tape drive, a ZIP drive, a RAM (Random Access Memory), and/or an other storage device, for example. The memory at the data source 110 preferably includes files, such as images, reports, applications, and/or other data, for example. Files at the data source 110 preferably are organized into at least one directory.

The data source 110 preferably also includes a processor capable of initiating at least one of several operation requests, such as an archive request, a restore request, and/or a copy request. As further described below, an archive request, for example, is a request to store data at the remote data store 120. Additionally, a restore request, for example, is a request to retrieve data stored at the remote data store 120. Also, a copy request is a request to copy data stored by another data source 115 at the remote data store 120 to the data source 110, for example.

Preferably, the remote data store 120 is an application service provider, but the remote data store 120 may be a server, a redundant disk array, a RAID (Redundant Array of Independent Disks) drive, a hard disk drive, an archive, a database system, a computer system, or other central data storage system, for example. The remote data store 120 has a capacity for data storage, such as a hard disk drive, a CD-ROM drive, a floppy disk drive, a tape drive, a ZIP drive, a RAM disk, and/or an other storage device, for example. The data storage preferably accommodates files, such as images, reports, applications, and/or other data, for example. Preferably, the files in the remote data store 120 are organized in directories corresponding to the data source 110. Preferably, the remote data store 120 also includes a processor capable of executing operations such as an archive operation, a restore operation, and/or a copy operation, for example. Additionally, the processor preferably may scan the directory of the data source 110. The processor may also examine files at the data source 10 and/or the remote data store 120. In an alternative embodiment, the remote data store 120 may be cached and stored at a plurality of locations.

In a preferred embodiment, the front-end connection 130 is a private network connection, such as a Digital Subscriber Line (DSL), a T1 line, an ISDN (Integrated Services Digital Network) line, an ATM (Asynchronous Transfer Mode) connection, a direct cable connection, or other private network, for example. Alternatively, the data source/data store connection 130 may be a dial-up modem connection (that is, via telephone line and computer modem), ethernet connection, the Internet, cable modem connection, wireless communication, a cable, a wire, or other network connection, for example. The front-end connection facilitates the bi-directional transmission and/or reception of files, commands, instructions, communication information, and/or other data, for example, between the data source 110 and the status monitor 140 and the access authenticator 145.

In a preferred embodiment, the back-end connection 135 is substantially similar to the front-end connection 130 described above. The back-end connection facilitates the bi-directional transmission and/or reception of files, commands, instructions, communication information, and/or other data, for example, between the remote data store 120 and the status monitor 140 and the access authenticator 145. Preferably, the front-end connection 130 and the back-end connection 135 compose a data source/data store connection to transfer data between the data source 110 and the remote data store 120.

In a preferred embodiment, the status monitor 140 monitors the data source 110, the remote data store 120, the front-end connection 130, and/or the back-end connection 135. That is, the status monitor 140 monitors and/or controls activities such as requests by the data source 110, requests by the remote data store 120, data at the data source 110, data at the remote data store 120, data traveling over the front-end connection 130 and/or the back-end connection 135, commands and/or instructions traveling over the front-end connection 130 and/or the back-end connection 135, for example. Preferably, the status monitor 140 includes a processor to monitor the data source 110, the remote data store 120, the front-end connection 130, and/or the back-end connection 135. Preferably, the status monitor 140 may transmit commands and/or instructions, for example, to the data source 110 and/or the remote data store 120. Additionally, the status monitor 140 preferably may receive commands and/or instructions, for example, from the data source 110 and/or the remote data store 120.

The access authenticator 145 authenticates access of the remote data store 120 by the data source 110. Additionally, the access authenticator 145 may authenticate access of the data source 110 by the remote data store 120. Preferably, the access authenticator 145 includes a predetermined authentication code or set of authentication codes (such as a database or table of codes, for example). For example, the access authenticator 145 preferably includes an authentication code input by a user, an authentication code generated daily, an authentication code generated monthly, a randomly generated authentication key, and/or other authentication code, for example. The access authenticator may receive an authentication code, such as a password, identification number, or other authentication code, for example, from the data source 110, the remote data store 120, and/or the status monitor 140. Preferably, the authentication code may be assigned according to an individual user, a group of users, a type of data source, a location, and/or a function, for example.

In a preferred embodiment, the front-end connection 130 connects the data source 110 to the status monitor 140 and the access authenticator 145. Preferably, the back-end connection 135 connects the remote data store 120 to the status monitor 140 and the access authenticator 145. The status monitor 140 may connect to the access authenticator 145 via a network connection, such as the Internet ethernet, direct cable connection, wireless, modem, wire, physical connection, or other network connection, for example. The location of the status monitor 140 with respect to the data source 110 and/or the remote data store 120 is not fixed. That is, the status monitor 140 may be located at the data source 110, the remote data store 120, and/or the access authenticator 145. Additionally, the location of the access authenticator 145 with respect to the data source 110 and/or the remote data store 120 is not fixed. That is, the access authenticator 145 may be located at the data source 110, the remote data store 120, and/or the status monitor 140.

As mentioned above, the data source 110 preferably includes a processor capable of initiating at least one of several operation requests, such as an archive request, a restore request, and/or a copy request. Each operation request is further discussed individually below. With respect to the archive operation request, the system 100 preferably operates as follows. First, data, such as an image or other medical data is obtained using medical diagnostic equipment and/or a healthcare practitioner. The image may be an x-ray image, an ultrasound image, a magnetic resonance image, or a computerized tomography image, for example. Other medical data may include examination reports, patient demographic data, and/or scheduling data, for example. The image of a patient may be obtained using medical diagnostic equipment, such as an x-ray imaging system, a magnetic resonance imaging system, or a computerized tomography imaging system, for example. For example, a patient visits a hospital for a computerized tomography (CT) scan, and a technician obtains the image using a computerized tomography imaging system. Then, the data is stored at the data source 110. For example, the technician stores the CT image of the patient at a PACS at the hospital.

Preferably, the status monitor 140 detects the storing of the data at the data source 110 via the front-end connection 130. Then, the status monitor 140 may prompt the data source 110 for an authentication code, which is discussed above. Next, the data source 110 transmits the authentication code to the access authenticator 145 via the status monitor 140. Then, the access authenticator 145 compares the received authentication code to the predetermined authentication code, which is discussed above. If the authentication code does not match the predetermined authentication code, then access to the remote data store 120 is not allowed. Alternatively, another attempt may be made to enter an authentication code. If the authentication code matches the predetermined authentication code, then the status monitor 140 triggers an archive request to be sent to the remote data store 120 via the back-end connection 135. For example, the status monitor 140 detects the storage of the computerized tomography image of the patient at the PACS and instructs the PACS to transmit the machine identification number of the PACS to the access authenticator 145. Then, for example, if the machine identification number matches an entry in the authentication code database of the access authenticator 145, the access authenticator 145 allows the status monitor 140 to trigger an archive request to the remote data store 120.

Next, the remote data store 120 receives the archive request. Then, the remote data store 120 processes the request. Preferably, the remote data store 120 determines if a directory exists at the remote data store 120 that corresponds to the data source 110. Then, the remote data store 120 and/or the status monitor 140 may determine which files from the data source 110 are up-to-date at the remote data store 120 and which files are to be transferred and stored at the remote data store 120. For example, the remote data store 120 locates the directory for the PACS at the remote data store 120. The status monitor 140, for example, then determines that the new CT image is not in the PACS directory at the remote data store 120.

Next, the status monitor 140 preferably instructs the data source 110 to transmit the data to be stored to the remote data store 120 via the front-end connection 130 and the back-end connection 135. For example, the status monitor 140 transmits instructions to the PACS directing the PACS to transmit the CT image to the remote data store 120. Then, the remote data store 120 archives the data sent by the data source 110 at the remote data store 120. Preferably, the data is archived at the remote data store 120 at the directory which corresponds to the data source 110. For example, the remote data store 120 stores the CT image file from the PACS in the PACS directory at the remote data store 120.

After the data is transferred between the data source 110 and the remote data store 120, the status monitor 140 may verify the transmission and/or receipt of the data. That is, the status monitor 140 may verify the transmission and/or receipt of the data by comparing file names, file sizes, file time stamps, file checksums, data transmission codes, and/or error correction codes, for example. For example, the status monitor may verify the transfer of the CT image from the PACS to the remote data store 120 by performing a cyclic redundancy check (CRC) on the data or by checking the parity bits of the transferred data, for example, to insure that data was not lost or corrupted during transmission.

In an alternative embodiment, the archive request may be triggered after a definable interval, such as a timed interval, an event-based interval, and/or another programmed interval. That is, a timed trigger may trigger an archive request hourly, daily, weekly, monthly, quarterly, and/or yearly, for example. For example, the PACS may be programmed to request an archive operation at the end of every day. Also, an event-based trigger may trigger an archive request after data is obtained, after data is saved, upon system shutdown, and/or upon program error, for example.

For a restore request, the system 100 preferably operates as follows. First, data, such as an image or other medical data is obtained and archived at the remote data store 120 as described above in relation to the archive operation. For example, an x-ray image of a patient and a radiology report for the patient are obtained and stored at a local PACS at a clinic. The image and report are then archived at the remote data store 120 in a directory corresponding to the PACS.

In a preferred embodiment, an operation attempts to access the data at the data source 110 and discovers an error in the data. For example, a user attempts to view the x-ray image and radiology report at the PACS and discovers that the image and report have been corrupted. Alternatively, the data source 110 may automatically discover the error in the data. Preferably, the status monitor 140 detects the error, such as data loss, data corruption, and/or system failure, for example, at the data source 110 via the front-end connection 130.

Then, the status monitor 140 may prompt the data source 110 for an authentication code, as discussed above. Next, the data source 110 transmits the authentication code to the access authenticator 145 via the status monitor 140. Then, the access authenticator 145 compares the received authentication code to the predetermined authentication code, as discussed above. If the authentication code does not match the predetermined authentication code, then access to the remote data store 120 is not allowed. Alternatively, another attempt may be made to enter an authentication code. If the authentication code matches the predetermined authentication code, then the status monitor 140 triggers a restore request to be sent to the remote data store 120 via the back-end connection 135. For example, the status monitor 140 detects corruption of the x-ray image at the PACS and instructs the PACS to transmit the monthly access password to the access authenticator 145. Then, for example, if the monthly access password matches the monthly password in the database of the access authenticator 145, the access authenticator 145 allows the status monitor 140 to trigger a restore request to the remote data store 120.

Next, the remote data store 120 receives the restore request. Then, the remote data store 120 processes the request. Preferably, the remote data store 120 determines if a directory exists at the remote data store 120 that corresponds to the data source 110. Next, the remote data store 120 determines if the lost and/or corrupted data is present in the directory at the remote data store 120. If the data is not present in the directory at the remote data store 120, then the restore operation is halted. If the data is present in the directory at the remote data store 120, then the data may be retrieved. For example, the remote data store 120 locates the directory for the PACS at the remote data store 120. Next, for example, the remote data store 120 determines that the x-ray image and the radiology report are stored at the directory for the PACS at the remote data store 120.

Next, the status monitor 140 preferably instructs the remote data store 120 to transmit the data to be restored to the data source 110 via the back-end connection 135 and the front-end connection 130. For example, the status monitor 140 transmits instructions to the remote data store 120 directing the remote data store 120 to transmit the x-ray image and radiology report to the PACS. Then, the data source 110 restores the data sent by the remote data store 120 at the data source 110. For example, the PACS stores the x-ray image file and radiology report from the PACS directory at the remote data store 120 at the PACS.

After the data is transferred between the remote data store 120 and the data source 110, the status monitor 140 may verify the transmission and/or receipt of the data. That is, the status monitor 140 may verify the transmission and/or receipt of the data by comparing file names, file sizes, file time stamps, file checksums, data transmission codes, and/or error correction codes, for example. For example, the status monitor may verify the transfer of the x-ray image and the radiology report from the remote data store 120 by performing a cyclic redundancy check (CRC) on the data or by checking the parity bits of the transferred data, for example, to insure that data was not lost or corrupted during transmission.

For a copy request, the system 100 preferably operates as follows. First, data, such as an image or other medical data is obtained, stored at a data source 115, and archived at the remote data store 120 as described above in relation to the archive operation. For example, an ultrasound image of a patient and an electrocardiogram (ECG) for the patient are obtained and stored at a local PACS at a clinic. The image and ECG are then archived at the remote data store 120 in a directory corresponding to the PACS.

Preferably, the status monitor 140 detects the installation of a new data source 110, such as an upgraded data source or a replacement data source, for example. Then, the status monitor 140 may prompt the data source 110 for an authentication code, as discussed above. Next, the data source 110 transmits the authentication code to the access authenticator 145 via the status monitor 140. Then, the access authenticator 145 compares the received authentication code to the predetermined authentication code, as discussed above. If the authentication code does not match the predetermined authentication code, then access to the remote data store 120 is not allowed. Alternatively, another attempt may be made to enter an authentication code. If the authentication code matches the predetermined authentication code, then the status monitor 140 triggers a copy request to be sent to the remote data store 120. For example, the status monitor 140 detects the connection of a newer PACS to the system 100 for upgrade and instructs the newer PACS to transmit the secure identification key to the access authenticator 145. Then, for example, if the secure identification key from the newer PACS matches the secure identification key in the database of the access authenticator 145, the access authenticator 145 allows the status monitor 140 to trigger a copy request to the remote data store 120.

Next, the remote data store 120 receives the copy request. Then, the remote data store 120 processes the request. Preferably, the remote data store 120 determines if a directory exists at the remote data store 120 that corresponds to the data source 115. Then, the status monitor 140 determines which data is to be copied to the data source 110. Next, the remote data store 120 determines if the data to be copied to the data source 110 is present in the directory for the data source 115 at the remote data store 120. For example, the remote data store 120 locates the directory for the PACS at the remote data store 120. The status monitor 140, for example, then determines that the ultrasound image and the ECG are to be copied to the newer PACS. Next, for example, the remote data store 120 determines that the ultrasound image and the ECG are stored at the directory for the PACS at the remote data store 120.

Next, the status monitor 140 preferably instructs the remote data store 120 to transmit the data to be copied to the data source 110. For example, the status monitor 140 transmits instructions to the remote data store 120 directing the remote data store 120 to transmit the ultrasound image and ECG to the newer PACS. Then, the data source 110 copies the data sent by the remote data store 120 at the data source 110. For example, the newer PACS stores the ultrasound image file and ECG from the PACS directory at the remote data store 120 at the newer PACS.

After the data is transferred between the remote data store 120 and the data source 110, the status monitor 140 may verify the transmission and/or receipt of the data. That is, the status monitor 140 may verify the transmission and/or receipt of the data by comparing file names, file sizes, file time stamps, file checksums, data transmission codes, and/or error correction codes, for example. For example, the status monitor may verify the transfer of the ultrasound image and the ECG from the remote data store 120 by performing a cyclic redundancy check (CRC) on the data or by checking the parity bits of the transferred data, for example, to insure that data was not lost or corrupted during transmission.

In an alternative embodiment, periodic copy operations may be executed to update the data source 110 with new data from the data source 115. Alternatively, the entire contents of the data source 115 may be copied to the data source 110 in a copy operation. In an alternative embodiment, the data from the data source 115 is deleted from the remote data store 120 after the data is copied to the data source 110.

In an alternative embodiment which may be applied to all of the above disclosed embodiments, the system 100 may comprise a plurality of data sources 110, 115. If multiple data sources 110, 115 attempt to access the remote data store 120 and/or if a single data source 110, 115 transmits multiple requests to the remote data store 120, the status monitor 140 may preferably arbitrate access to the remote data store 120. The status monitor 140 may arbitrate access to the remote data store 120 by allowing access to the remote data store 120 according to the priority of the data source 110, 115. Priority may include system priority, timing priority, or request priority, for example. For example, with system priority, a PACS may have a higher priority than an x-ray imaging system. With timing priority, for example, the system which has been waiting for the longest amount of time has a higher priority of access. For example, with request priority, a restore request may have a higher priority than a copy request. A data source 110, 115 may wait for access to the remote data store 120 until access is granted by the status monitor 140. For example, an ultrasound imaging system and an x-ray imaging system attempt to access the remote data store 120. The x-ray imaging system, for example, has a higher system priority than the ultrasound imaging system and is thus allowed to access the remote data store 120 first. The ultrasound imaging system waits for the remote data store 120 to complete the request of the x-ray imaging system and then the ultrasound imaging system may access the remote data store 120. Alternatively, the system 100 may accommodate multiple requests and/or multiple data sources. Alternatively, the system 100 may arbitrate command execution rather than access.

Figure 2:
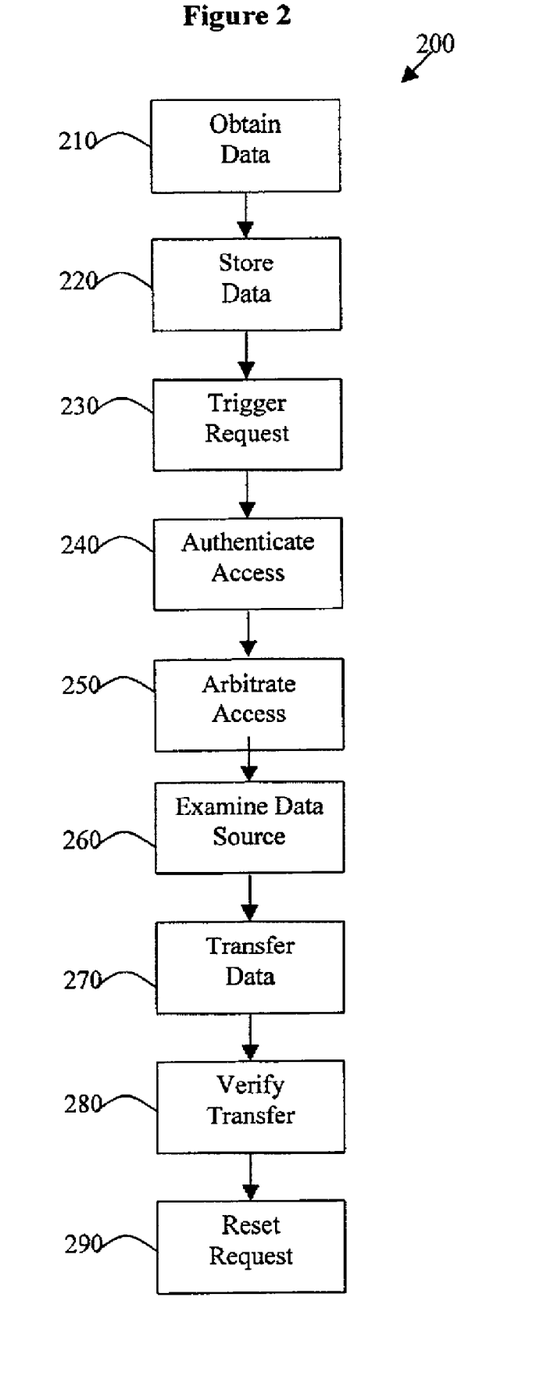
FIG. 2 illustrates a flowchart for archiving data from a data source at a remote data store in accordance with a preferred embodiment of the present invention.

FIG. 2 illustrates a flowchart 200 for archiving data from a data source at a remote data store in accordance with a preferred embodiment of the present invention. The data source may be a picture archiving and communications system (PACS), a medical diagnostic imaging system, a database system, a computer system, a server, a hard disk drive, a terminal, or other data storage system, for example. The remote data store may be an application service provider, a server, a redundant disk array, a RAID drive, a hard disk drive, an archive, a database system, a computer system, or other central data storage system, for example.

First, at step 210, data is obtained from a patient. Data may include an image (such as an x-ray image, an ultrasound image, a computerized tomography image, and/or a magnetic resonance image, for example) and/or other medical data (such as examination reports, electrocardiograms, patient demographic data, and/or scheduling data, for example). Data may be obtained using medical diagnostic equipment and/or examination by a healthcare professional, for example. For example, an x-ray image of a patient is obtained at a hospital. Next, at step 220, the data is stored at the data source. For example, the patient's x-ray image is stored in a PACS at the hospital.

Then, at step 230, an archive request is triggered. The archive request may be triggered by a status monitor, by the data source, and/or by the remote data source, for example. The request may preferably be triggered by programmed trigger and/or by manual trigger, for example. Preferably, a programmed trigger may trigger a request after a time interval (such as hourly, daily, monthly, yearly, etc.), an event (such as file creation, data storage, system failure, program error, and/or system shutdown, for example), or other such definable interval. For example, the status monitor detects the storage of the x-ray image in the PACS and triggers a request to archive the x-ray image.

Next, at step 240, the identity of the data source is authenticated to verify that the data source may access the remote data store. Preferably, authentication is facilitated using an authentication code, such as an authorization code, a personal identification number, a machine identification number, a password, or other identification code, for example. Preferably, the authentication code is transmitted automatically by the data source or input by a user, for example, after prompting by the status monitor. If the authentication code does not match a predetermined authentication code (such as a daily generated code, a monthly generated code, a random key, or other predetermined authentication code, for example), access is not granted. Alternatively, another attempt may be made to authenticate the access. If the authentication code matches the predetermined authentication code, the authentication code is verified, and access to the remote data store is authorized. For example, the status monitor prompts a technician at the PACS to enter a password to access the remote data store. Then, for example, the password is compared to the preset monthly password. If the technician's password matches the preset monthly password, the PACS may access the remote data store.

Then, at step 250, if multiple data sources are attempting to access a single remote data store, access to the remote data store may be arbitrated or controlled. Access arbitration may be facilitated by allowing access to the remote data store according to priority. Priority may include system priority, timing priority, or request priority, for example. That is, system priority indicates that one system has a higher priority of access than another system. Also, timing priority indicates that the system that has been waiting for access for the longest amount of time has a higher priority of access. Additionally, request priority signifies that certain operation requests may have a higher priority of access than other operation requests. Preferably, data sources may wait for access to the remote data store until access is granted through access arbitration. For example, the PACS and an x-ray system attempt to access the remote data store. The PACS, for example, initiates the access before the x-ray system and thus is first in time. Therefore, for example, the PACS is allowed to access the remote data store first. The x-ray system, for example, waits for the remote data store to complete the archive request of the PACS and then may access the remote data store. Alternatively, multiple accesses may be allowed at the remote data store.

Next, at step 260, the data source is examined to determine which data is to be archived at the remote data store. The status monitor, the data source, and/or the remote data store may determine which data is new or updated data to be archived at the remote data store and which data has already been archived at the remote data store. For example, the status monitor examines the directory of the PACS and locates the new x-ray image file to be archived at the remote data store. Alternatively, all data at the data source may be selected for archiving at the remote data store. Additionally, a user at the data source may manually select the data to archive at the remote data store (such as by clicking on file names in a backup program, for example).

Then, at step 270, the data is transferred from the data source to the remote data store. That is, files stored at the data source are transmitted to the remote data store. Preferably, the remote data store includes a directory, for example, in which to archive data from the data source. Alternatively, the remote data store includes a hard disk drive and/or other storage area, for example, in which to archive data from the data source. In the event of an archive request, data may be transferred from the data source to the directory, for example, of the remote data store to backup data and provide data reliability and security, for example. For example, the x-ray image file is transferred from the PACS to a directory at the remote data store which corresponds to the PACS. Data may be transmitted on a file-by-file basis, on a disk-by-disk basis, on a data block-by-data block basis, or on a bit-by-bit basis, for example.

Next, at step 280, the transfer of data between the data source and the remote data store is verified. That is, the data transfer may be verified by comparing file names, file sizes, file time stamps, file checksums, data transmission codes, and/or error correction codes, for example. For example, the status monitor may verify the transfer of the x-ray image file from the PACS to the remote data store by performing a cyclic redundancy check (CRC) on the file or by checking the parity bits of the transferred data, for example, to insure that data was not lost or corrupted during transmission.

Finally, at step 290, the triggered request is reset so that a new request may be triggered. For example, the status monitor signal to initiate an archive operation is reset to normal upon completion of the backup and verification that the PACS data has been archived at the remote data store.

Figure 3:
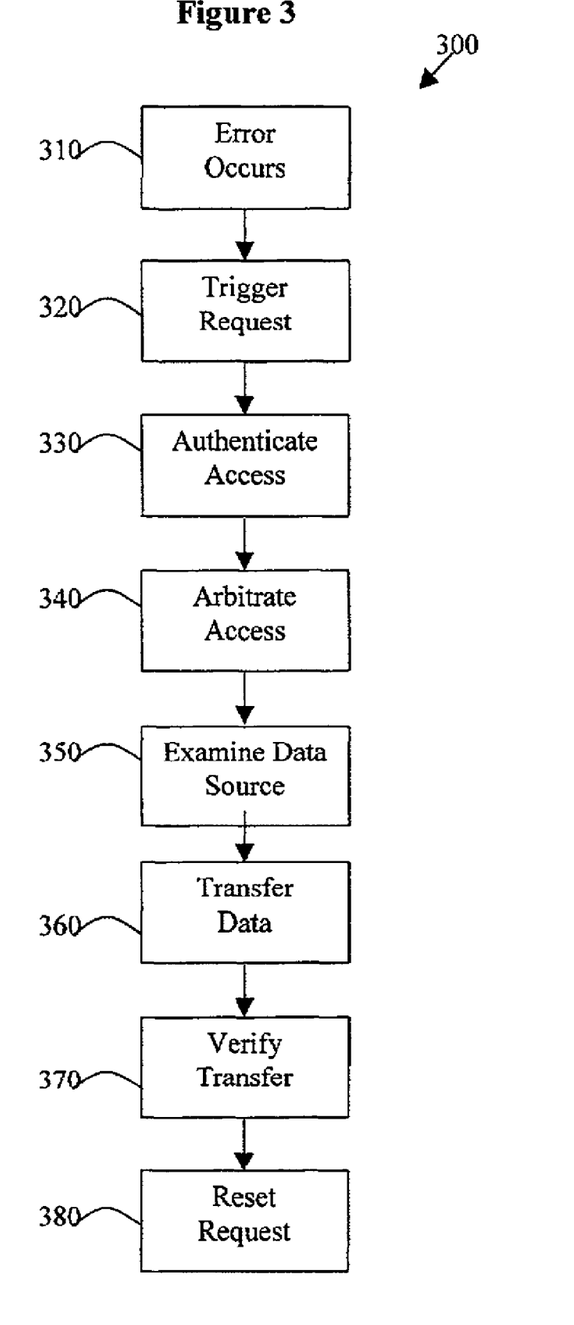
FIG. 3 illustrates a flowchart for restoring data from a remote data store to a data source in accordance with a preferred embodiment of the present invention.

FIG. 3 illustrates a flowchart 300 for restoring data from a remote data store to a data source in accordance with a preferred embodiment of the present invention.

First, data is obtained and archived at the remote data store in a method substantially similar to that described above in relation to FIG. 2. The data is preferably archived at the remote data store in a directory corresponding to the data source, as described above. Then, at step 310, an error occurs at the data source. The error may include data loss, data corruption, system failure, program error, and/or power loss, for example. For example, an x-ray image is corrupted in a PACS and is unviewable.

Then, at step 320, a restore request is triggered. The restore request may be triggered by a status monitor, by the data source, and/or by the remote data source, for example. The request may preferably be triggered by programmed trigger and/or by manual trigger, for example. Preferably, a programmed trigger may trigger a request after an event, such as system failure, data corruption, data loss, and/or program error, for example, occurs. For example, a user attempts to access the x-ray image at the PACS and discovers that the x-ray image is corrupted. The status monitor, for example, detects the corrupted x-ray image in the PACS and triggers a request to restore the x-ray image.

Next, at step 330, the identity of the data source is authenticated to verify that the data source may access the remote data store. Preferably, authentication proceeds as described above in reference to FIG. 2. For example, the status monitor prompts a technician at the PACS to enter a password to access the remote data store. Then, for example, the password is compared to the preset monthly password. If the technician's password matches the preset monthly password, the PACS may access the remote data store.

Then, at step 340, if multiple data sources are attempting to access a single remote data store, access to the remote data store may be arbitrated or controlled. Access arbitration may be facilitated by allowing access to the remote data store according to priority, as described above in reference to FIG. 2. Preferably, data sources may wait for access to the remote data store until access is granted through access arbitration. For example, the PACS and an x-ray system attempt to access the remote data store. The restore request of the PACS, for example, has a higher priority than the archive request of the x-ray system, and, thus, the PACS is allowed to access the remote data store first. The x-ray system, for example, waits for the remote data store to complete the restore request of the PACS and then may access the remote data store. Alternatively, multiple accesses may be allowed at the remote data store.

Next, at step 350, the data source is examined to determine which data is to be restored from the remote data store. The status monitor, the data source, and/or the remote data store may determine which data is lost or corrupted data to be restored at the data source and which data is already present at the data source. For example, the status monitor examines the directory of the PACS and locates the corrupted x-ray image file to be restored. Alternatively, a user at the data source may manually select the data to restore from the remote data store (such as by clicking on file names in a restore program, for example).

Then, at step 360, the data is transferred from the remote data store to the data source. That is, files stored at the remote data store are transmitted to the data source. Preferably, the remote data store includes a directory, for example, which contains data from the data source. Alternatively, the remote data store includes a hard disk drive and/or other storage area, for example, which contains data from the data source. In the event of a restore request, data may be transferred from the directory, for example, of the remote data store to the data source. For example, the x-ray image file is transferred to the PACS from the directory at the remote data store which corresponds to the PACS. Data may be transmitted on a file-by-file basis, on a disk-by-disk basis, on a data block-by-data block basis, or on a bit-by-bit basis, for example. Preferably, the data is not deleted from the remote data store after transfer and may be used again to restore at the data source 110.

Next, at step 370, the transfer of data between the remote data store and the data source is verified. That is, the data transfer may be verified by comparing file names, file sizes, file time stamps, file checksums, data transmission codes, and/or error correction codes, for example. For example, the status monitor may verify the transfer of the x-ray image file from the remote data store to the PACS by performing a cyclic redundancy check (CRC) on the file or by checking the parity bits of the transferred data, for example, to insure that data was not lost or corrupted during transmission.

Finally, at step 380, the triggered request is reset so that a new request may be triggered. For example, the status monitor signal to initiate a restore operation is reset to normal upon completion of the restore and verification that the data has been restored at the PACS.

Figure 4:
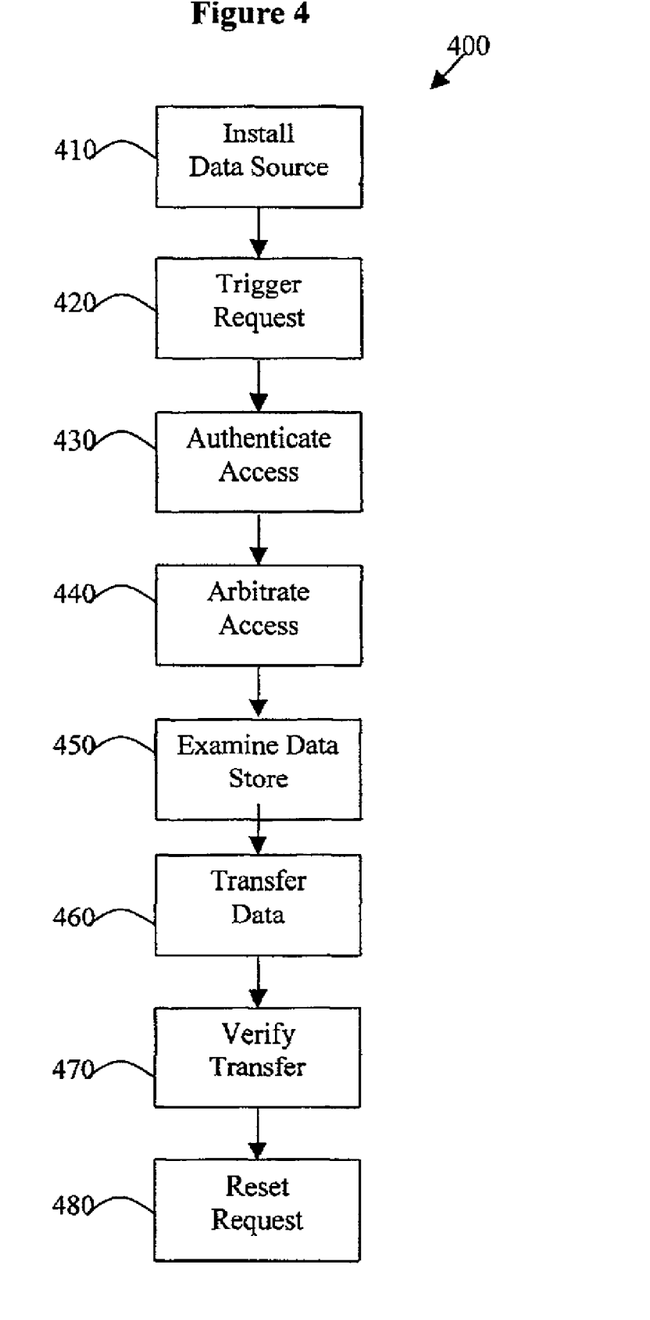
FIG. 4 illustrates a flowchart for copying data from a remote data store to a data source in accordance with a preferred embodiment of the present invention.

FIG. 4 illustrates a flowchart 400 for copying data from a remote data store to a data source in accordance with a preferred embodiment of the present invention. First, data is obtained from a first data source and archived at the remote data store in a method substantially similar to that described above in relation to FIG. 2. The data is preferably archived at the remote data store in a directory corresponding to the first data source, as described above. Then, at step 410, a second data source is installed. That is, an additional, upgraded, and/or replacement data source may be added along with or in place of the first data source. For example, a hospital upgrades their data storage capabilities and installs a new PACS to replace the old PACS.

Then, at step 420, a copy request is triggered. The copy request may be triggered by a status monitor, by the first data source, by the second data source, and/or by the remote data source, for example. The request may preferably be triggered by programmed trigger and/or by manual trigger, for example. Preferably, a programmed trigger may trigger a request after an event (such as system start-up, system installation, and/or connection to the network, for example), or other such definable interval. For example, the status monitor detects the presence of the new PACS and triggers a request to copy the data from the old PACS to the new PACS.

Next, at step 430, the identity of the second data source is authenticated to verify that the second data source may access the remote data store. Preferably, authentication proceeds as described above in reference to FIG. 2. For example, the status monitor prompts a technician at the new PACS to enter a password to access the remote data store. Then, for example, the password is compared to the preset monthly password. If the technician's password matches the preset monthly password, the new PACS may access the remote data store.

Then, at step 440, if multiple data sources are attempting to access a single remote data store, access to the remote data store may be arbitrated or controlled. Access arbitration may be facilitated by allowing access to the remote data store according to priority, as described above in reference to FIG. 2. Preferably, data sources may wait for access to the remote data store until access is granted through access arbitration. For example, the new PACS and an x-ray system attempt to access the remote data store. The PACS, for example, has a higher system priority than the x-ray system, and, thus, the PACS is allowed to access the remote data store first. The x-ray system, for example, waits for the remote data store to complete the copy request of the PACS and then may access the remote data store. Alternatively, multiple accesses may be allowed at the remote data store.

Next, at step 450, the remote data store is examined to determine which data is to be copied from the remote data store to the second data source. The status monitor, the data source, and/or the remote data store may determine which data is to be copied from the remote data store to the second data source and which data is already present or unnecessary at the second data source. Preferably, the remote data store includes a directory, for example, which contains data from the first data source. Alternatively, the remote data store may include a hard disk drive and/or other storage area, for example, which contains data from the first data source. Thus, the directory, for example, which contains data from the first data source may be examined to determined which data is to be copied to the second data source. For example, the status monitor examines the directory of the remote data store and locates the directory containing files from the old PACS. Alternatively, a user at the data source may manually select the data to copy from the remote data store (such as by clicking on file names in a copy program, for example).

Then, at step 460, the data is transferred from the remote data store to the second data source. That is, files stored at the remote data store are transmitted to the second data source. In the event of a copy request, data may be transferred from the directory, hard disk drive, and/or storage area, for example, of the remote data store which corresponds to the first data source to the second data source. For example, data in the directory of the remote data store corresponding to the first data source is transferred to the second data source. Data may be transmitted on a file-by-file basis, on a disk-by-disk basis, on a data block-by-data block basis, or on a bit-by-bit basis, for example. Preferably, the data is not deleted from the remote data store after the data is copied to the second data source.

Next, at step 470, the transfer of data between the remote data store and the second data source is verified. That is, the data transfer may be verified by comparing file names, file sizes, file time stamps, file checksums, data transmission codes, and/or error correction codes, for example. For example, the status monitor may verify the transfer of the files from the remote data store to the PACS by performing a cyclic redundancy check (CRC) on the file or by checking the parity bits of the transferred data, for example, to insure that data was not lost or corrupted during transmission.

Finally, at step 480, the triggered request is reset so that a new request may be triggered. For example, the status monitor signal to initiate a copy operation is reset to normal upon completion of the copy operation and verification that the data has been copied to the new PACS.

In an alternative embodiment, periodic copy operations may be executed to update the second data source with new data from the first data source. Alternatively, the entire contents of the first data source may be copied to the second data source in a copy operation. In an alternative embodiment, the data from the first data source is deleted from the remote data store after the data is copied to the second data source.

Thus, the preferred embodiments of the present invention provide centralized archiving and retrieval of medical data via a remote data store. That is, a data source may archive data at the remote data store and retrieve the data in the event of a system failure, file corruption, or data loss, for example. Additionally, the preferred embodiments provide for retrieval of data from a central remote data store at multiple locations. For example, a first hospital with a first PACS may archive the data from the first PACS at the remote data store. Then, a second hospital with a second PACS may copy the data from the remote data store onto the second PACS. Thus, the files may be reliably retrieved and accessed at a variety of locations via the remote data store.

Thus, the preferred embodiments allow reliable access to medical data by providing a remote data store to archive data from a data source and restore data at the data source. That is, in the event of data loss and/or corruption, the data may be restored at the data source by the remote data store. Additionally, in the event of a system failure, the data at the remote data store may be copied to a replacement system. Thus, the preferred embodiments provide reliable access to medical data to aid in the diagnosis and treatment of patients by helping to insure that data is available so that healthcare practitioners may use the data to aid in the diagnosis and treatment of patients.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for remotely accessing a centralized data store, said system comprising:

A centralized remote data store medical data indexed according to data source, wherein said medical data comprises at least one of a medical image, a medical report, and a medical application, wherein said centralized remote data store comprises an application service provider; and A status monitor for controlling a transfer of said medical data from said centralized remote data store to a data source, wherein said status monitor automatically detects an error in said data source by detecting at least one of data loss, data corruption, and failure of said system via a front-end connection between said data source and said status monitor, said status monitor instructing said centralized remote to transmit data to said data source in order to restore said medical data, Wherein said source received said medical data and stored said medical data.

2. The system of claim 1, further comprising a second data source storing medical data.

3. The system of claim 2, wherein said status monitor controls the transfer of said copy of said medical data between said remote data store and said second data source.

4. The system of claim 2, wherein said status monitor verifies the transfer of said copy of said medical data between said remote data store and said second data source.

5. The system of claim 1, further comprising an access authenticator for authenticating access to said remote data store.

6. The system of claim 1, wherein said status monitor verifies said transfer of said medical data between said data source and said remote data store.

7. The system of claim 1, wherein said remote data store restores said medical data at said data source.

8. The system of claim 1, wherein said remote data store comprises at least one directory corresponding to said data source.

9. The system of claim 1, further comprising a privately network connection for transferring said medical data between said data source and said centralized remote data store.

* * * * *